US000001473H

United States Statutory Invention Registration [19]

[11] Reg. Number: H1473

Orofino et al.

[43] Published: Aug. 1, 1995

[54] CLEAR ANTIPERSPIRANT STICKS

[76] Inventors: Steven A. Orofino, 1156 Wells Pl., Stratford, Conn. 06497; Matthew F. Kuznitz, 144 Austin Ryer La., Branford, Conn. 06405

[21] Appl. No.: 216,111

[22] Filed: Mar. 22, 1994

[51] Int. Cl.[6] ..... A61K 7/36; A61K 7/32

[52] U.S. Cl. ..... 424/67; 424/65

[58] Field of Search ..... 424/65, 67

*Primary Examiner*—Shean Wu

[57] ABSTRACT

Antiperspirant compositions in gel form are provided which include an antiperspirant-active salt, a $C_2$–$C_6$ polyhydric alcohol, dibenzyl monosorbitol acetal, and a borate salt, especially anhydrous borax. The borate salt serves as a stabilizer for the gelled stick.

4 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

CLEAR ANTIPERSPIRANT STICKS

BACKGROUND OF THE INVENTION

1. Field of the Invention

The invention relates to antiperspirant compositions in the form of gelled sticks.

2. The Related Art

Cosmetic sticks which exhibit a clear appearance can be prepared using sodium stearate as a gelling agent or structurant. Unfortunately, these clear sticks cannot be formulated with antiperspirant-active salts because the alkaline gelling agents will react with the acidic salts. This incompatibility has been surmounted through use of neutral structurants, for instance, use of low melting waxy materials such as stearyl alcohol. Stability is good but the resultant sticks are opaque.

For many years, the art has investigated a unique gelling agent known as dibenzyl monosorbitol acetal (DBMSA) for use in translucent or transparent sticks. No derivative of sorbitol or any other gelling agent has yet been found which equals its structurant properties. However, it is also known that acetals are stable only in alkaline or neutral media, but not in acidic media. Under an acidic environment even in the presence of small amounts of water, the acetal hydrolyzes or will react with alcohol, e.g. ethanol, to form a different acetal.

Thus, antiperspirant sticks containing acidic antiperspirant-active salts in the presence of DBMSA in reactive alcoholic solvents have not been satisfactory because, in time, especially at elevated temperatures, they deteriorate and liquify. There is a need, therefore, to find a way to stabilize these sticks against such deterioration.

Antiperspirant sticks containing dibenzyl monosorbitol acetal and antiperspirant-active salts are disclosed in U.S. Pat. No. 4,154,816 (Roehl et al.). These sticks contain, in addition to the antiperspirant-active salt and DBMSA, a lower monohydric alcohol, a di- or trihydric alcohol, a propylene-/ethylene-glycol polycondensate, and optionally an alkylolamide. A problem with these products is their stickiness on application. U.S. Pat. No. 4,346,079 (Roehl) reports elimination or significant reduction of the stickiness problem through replacement of at least part of the polycondensate with an oleaginous compound.

U.S. Pat. No. 4,518,582 (Schamper et al.) found that the Roehl antiperspirant sticks, even with the improved stickiness control, were not stable on extended exposure at elevated temperatures. The problem was addressed through use of a gel stabilizer such as magnesium sulfate, zinc acetate and hexamethylenetetramine. Another remedy for stickiness is disclosed in U.S. Pat. No. 4,720,381 (Schamper et al.) wherein non-reactive solvents were used to replace reactive ones. Less reactive alcohols were identified as isopropanol, isobutanol, dipropylene glycol and other higher molecular weight alcohols. A still further approach was described in U.S. Pat. No. 4,725,430 (Schamper et al.) wherein N-(2-hydroxyethyl) acetamide was utilized as a stabilizing agent in the gel.

Another refinement of the DBMSA system is reported in U.S. Pat. No. 4,781,917 (Luebbe et al.) which utilizes a coupling agent and buffering adjustment agent to improve the stick. The coupling agent may be a polypropylene glycol (PPG) ether of a $C_4$–$C_{22}$ fatty alcohol. Suitable buffering adjustment agents were stated to be coconut monoethanolamide, sodium aluminum chlorohydroxylactate, sodium hydroxide, stearamide monoethanolamide, acetamide MEA, zinc acetate, zinc oxide, zinc stearate, zinc carbonate and similar materials.

U.S. Pat. No. 4,743,444 (McCall) describes improvements in gel rheology and transparency, while maintaining hardness and physical integrity. These benefits were obtained by incorporation of a $C_{14}$–$C_{16}$ fatty alcohol.

U.S. Pat. No. 4,719,102 (Randhawa et al.) in conjunction with a DBMSA gel stick describes novel solvents for use therein to allow processing at lower temperatures. The novel solvent is a compound having not greater than about five carbon atoms that includes, for instance, morpholine, pyridine, acetic acid, ethylene carbonate, propylene carbonate, etc.

EP 0 512 770 A1 (Benfatto et al.) describes DBMSA compositions wherein water and lower monohydric alcohols have been replaced with dihydroxy aliphatic alcohols containing 3 to 6 carbon atoms as solvents.

Westwood Chemical Corporation in its data sheets has suggested that a DBMSA gel stick could be stabilized with zinc glycinate. At higher temperatures this technology is insufficiently effective to prevent cloudiness arising in the gel stick. Clarity is especially adversely effected when the compositions contain emollients necessary to improve product aesthetics and avoid the tacky feel associated with this type of formulation.

Accordingly, it is an object of the present invention to provide an antiperspirant stick gelled with DBMSA which does not deteriorate or become sticky, even at higher temperatures.

Another object of the present invention is to provide an antiperspirant stick gelled with DBMSA that not only is stable but has good clarity, i.e. at least translucent if not transparent.

Still another object of the present invention is to provide an antiperspirant stick gelled with DBMSA that includes emollients yet minimizes the tacky feel commonly associated with these types of formulations.

These and other objects of the present invention will become more readily apparent from consideration of the following summary, examples and detailed description.

SUMMARY OF THE INVENTION

An antiperspirant composition is provided which includes:

(i) from about 1 to about 50% by weight of an antiperspirant-active salt;

(ii) from about 5 to about 60% of a $C_2$–$C_{12}$ polyhydric alcohol;

(iii) from about 0.5 to about 10% of dibenzyl monosorbitol acetal; and (iv) from about 0.1 to about 20% of a borate salt that when combined with other components of the composition will result in a pH of at least 4.3 for the composition.

The borate salts function to stabilize the gelled stick. Most efficacious are the anhydrous borates of relatively alkaline character such as disodium tetraborate (anhydrous borax).

DETAILED DESCRIPTION OF THE INVENTION

Now it has been discovered that the tackiness and aesthetics of a DBMSA gelled antiperspirant stick can be improved through the addition of borate salts. Thus, the essential components of gelled sticks according to the present invention are an antiperspirant-active salt, at least one polyhydric alcohol as solvent, DBMSA as gellant and the borate salts.

Accordingly, the first necessary element of compositions according to the present invention is an antiperspirant-active salt. Actives within this category include: polyhydroxy complexes of basic aluminum salts (e.g. aluminum chlorohydrol-propylene glycol complex), polyhydroxy derivatives of zinc and zirconium complexes of basic aluminum halides, zirconal hydroxychloride salts (e.g. zirconium/aluminum glycine complexes known as "ZAG"), aluminum chlorhydroxide, aluminum chloride, aluminum sesquichlorhydroxide and activated aluminum chlorhydroxide.

Levels of the antiperspirant-active salt may range from about 1 to about 50%, preferably from about 10 to about 40%, optimally between about 15 and about 30% by weight.

A second necessary element of compositions according to the present invention is that of a polyhydric alcohol functioning as a solvent for the composition. Polyhydric alcohols may be selected from the group consisting of 1,2-propylene glycol; 1,3-propylene glycol; 1,3-butylene glycol; glycerin; 2-methyl-2,4-pentane-diol; 2-ethyl-1,3-hexane-diol; 1,4-dihydroxypentane; 1,4-butylene glycol; dipropylene glycol; dibutylene glycol and mixtures thereof. Levels of polyhydric alcohol may range from about 5 to about 60%, preferably from about 10 to about 50%, optimally between about 25 and 40% by weight.

Dibenzyl monosorbitol acetal to be utilized in compositions of the present invention are commercially available as Millithix 925 from Milliken Chemical, Division of Milliken & Company and as Gell A-D from the New Japan Chemical Company, Ltd., Osaka, Japan. Levels of DBMSA should range from about 0.5 to about 10%, preferably from about 1.5 to about 5%, optimally between about 1.8 and 3% by weight.

The improvement element of compositions according to the present invention is a stabilizer for DBMSA to maintain the gelled stick structure. The stabilizer is a borate salt, preferably anhydrous and with a relatively high pH to allow the composition to reach a pH of at least 4.3. Most preferred for use in this invention is anhydrous borax technically identified as disodium tetraborate of formula $Na_2O$ $2B_2O_3$. Less preferred but also useful are disodium tetraborate decahydrate (borax), disodium tetraborate pentahydrate, disodium tetraborate tetrahydrate, dicalcium hexaborate pentahydrate, dipotassium tetraborate tetrahydrate, disodium octaborate tetrahydrate, potassium pentaborate tetrahydrate, sodium calcium pentaborate octahydrate, sodium calcium pentaborate pentahydrate, sodium metaborate dihydrate, sodium metaborate tetrahydrate, sodium pentaborate pentahydrate, diammonium tetraborate tetrahydrate and combinations thereof. Levels of the borate salt will range from about 0.1 to about 20%, preferably from about 0.4 to 5%, optimally from about 0.8 to about 2% by weight.

A variety of buffering/pH adjustment agents may also be incorporated into compositions according to the present invention. Illustrative of this category are coconut monoethanolamide, sodium hydroxide, sodium carbonate, sodium bicarbonate, potassium hydroxide, potassium carbonate, potassium bicarbonate, magnesium oxide, magnesium hydroxide, magnesium carbonate, stearamide monoethanolamide, acetamide MEA, calcium carbonate, calcium oxide, aluminum oxide, calcium acetate, zinc glycinate, zinc oxide, zinc acetate and mixtures thereof. Most preferred is zinc glycinate. Levels of these agents may range from about 0.1 to about 10%, preferably from about 0.4 to about 3%, optimally from about 0.5 to about 1.5% by weight.

Emollients and coupling agents may also be included in compositions according to the present invention. Often, materials will function both as emollient and coupling agent. Illustrative of these materials are $C_6$–$C_{22}$ fatty alcohols, ethoxylated derivatives of $C_6$–$C_{22}$ fatty alcohols, propoxylated derivatives of $C_6$–$C_{22}$ fatty alcohols, and mixtures thereof. Specific examples of these are: PPG-5-ceteth-20; PPG-4 myristyl ether; PPG-4 lauryl ether; PPG-10 cetyl ether; PPG-3 myristyl ether; Glycereth 7; PPG-10 butane diol and mixtures thereof. Most preferred is PPG-10 butane diol (available as Macol 57) and Glycereth 7 (available as Liponic EG-7). Levels of these materials may range from about 0.1 to about 20%, preferably from about 0.5 to about 10%, optimally from about 0.8 to about 3% by weight.

Co-gellants may also be included in compositions according to the present invention. Particularly preferred are the ethylene oxide/propylene oxide copolymers such as Pluronic F77 available from the BASF Corporation. Amounts of these materials may range from 0.1 to about 5%, preferably from about 0.3 to about 3%, optimally from about 0.5 to about 1% by weight.

Volatile and nonvolatile silicone oils may also be incorporated into compositions according to the present invention. Preferred silicones include the polydimethyl siloxanes having from 3 to about 9 silicon atoms. Examples of silicone oils useful herein include: Dow Corning 344, Dow Corning 345 and Dow Corning 200. Silicone copolyols may also be useful, a preferred material being commercially available as Amersil DMC 357. Amounts of these materials may range from about 0.1 to about 20%, preferably from about 0.2 to about 3%, optimally between about 0.4 and 1.5% by weight.

Adjunct components of compositions according to the present invention may include fragrances, colorants, sunscreens, bacteriostats and combinations thereof, each at a level sufficient to perform their function. Generally, these materials will be present in amounts anywhere from about 0.01 to about 5% by weight of the compositions.

Sticks according to the present invention will preferably be clear. By the term clear is meant either translucent or transparent. Typically, the clear sticks will allow at least 2%, preferably more than 10%, optimally more than 50% of light to be transmitted through a one inch diameter stick.

The following Examples will more fully illustrate embodiments of this invention. All parts, percentages and proportions referred to herein and in the appended claims are by weight unless otherwise indicated.

EXAMPLE 1

A composition according to the present invention is described in the following Table.

TABLE I

| COMPONENT | % WEIGHT |
|---|---|
| Propylene Glycol | 58.95 |
| Dipropylene Glycol | 18.00 |
| Al/Zr Tetrachlorohydrate Glycol Powder | 12.00 |

TABLE I-continued

| COMPONENT | % WEIGHT |
|---|---|
| PPG-3-Myristyl Ether | 3.00 |
| Dibenzylidene Monosorbitol Acetal | 2.50 |
| Glycereth-7-Benzoate | 1.50 |
| PPG-3-Isostearetb-9 | 1.50 |
| Anhydrous Borax | 0.90 |
| Glycerin USP | 0.75 |
| Perfume | 0.50 |
| FD&C #1 (0.1% Propylene Glycol Solution | 0.40 |
| Total | 100.00 |

The procedure for preparing the composition is as follows:

1. Add 29.95 parts of Propylene Glycol to a suitable vessel equipped with a Premier Mixer and a Cowles Dissolver. Heat to 93° C.

2. Add Al/Zr Tetrachlorohydrate Gly-Propylene Glycol Powder and mix until clear.

3. Add 29 parts of Propylene Glycol and Anhydrous Borax to a separate vessel and heat to 115° C. Mix until clear.

4. Add the composition formed in Step 3 to that formed in Step 2 and heat to 115° C. while mixing.

5. Add Dibenzylidene Monosorbitol Acetal-925 (sieved) slowly to the batch and mix until clear. Add glycerin and mix for 15 minutes.

6. Cool the batch to 93° C.

7. Add Dipropylene Glycol, Glycereth-7-Benzoate, PPG-3-Isostearetb-9, PPG-3-Myristyl Ether and FD&C Blue #1 solution to a separate vessel and heat to 93° C.

8. Add the composition prepared in Step 7 at 93° C. to the composition of Step 6 at 200° F. Cool to 80° C. to 82° C. while mixing.

9. Add perfume to batch at 80° C. to 82° C. and mix gently.

10. Pour the product into containers when the batch is 70° C. to 75° C.

EXAMPLE 2

A composition according to the present invention is described in the following Table.

TABLE II

| COMPONENT | % WEIGHT |
|---|---|
| Propylene Glycol | 63.57 |
| Dipropylene Glycol | 18.00 |
| Aluminum Chlorohydrate-Propylene Glycol Complex | 12.00 |
| Dibenzylidene Monosorbitol Acetal | 2.25 |
| Dimethicone Copolyol | 1.50 |
| Glycereth-7-Benzoate | 0.75 |
| Anhydrous Borax | 0.63 |
| Glycerin, USP | 0.50 |
| Perfume | 0.50 |
| Color FD&C Blue #1 (0.1% Propylene Glycol Solution) | 0.30 |
| Total | 100.00 |

The procedure for preparing the composition is as follows:

1. Add 34.75% of the formula weight of Propylene Glycol into a suitable mixing vessel and begin to heat to 115° C. Add ACH - Propylene Glycol Complex and mix with a Premier mixer attached with a Cowles dissolver. Continue mixing for the entire manufacturing process.

2. Add 29% of the formula weight of Propylene Glycol into a suitable mixing vessel and begin to heat to 115° C. Add anhydrous borax and mix until a clear solution is obtained. Add to batch at 115° C. and mix batch rapidly for 15 minutes at the same temperature.

3. Add Dibenzylidene Monosorbitol Acetal 925 slowly to batch at 115° C. Maintain this temperature for 45 minutes while mixing rapidly. Cool batch to 100° C. while mixing gently.

4. Add Dipropylene Glycol, Glycerin, Glycereth-7-Benzoate, Dimethicone Copolyol-193, and FD&C Blue #1 (0.1% Propylene Glycol Solution) to a separate vessel and heat to 100° C.

5. Add Step 4 components to batch and cool to 82° C. while mixing gently.

6. Add perfume at batch temperature of 82° C. while mixing gently.

7. Pour into containers.

EXAMPLES 3-9

A further series of compositions according to the present invention are reported in the table below.

| | WEIGHT % | | | | | | |
|---|---|---|---|---|---|---|---|
| COMPONENT | 3 | 4 | 5 | 6 | 7 | 8 | 9 |
| Rehydrol II | 51 | 42 | 41 | 41 | 51 | 51 | 51 |
| Dipropylene Glycol | 24 | 24 | 22 | 22 | 10 | 10 | 24 |
| Propylene Glycol | 15 | 15 | 15 | 15 | 29 | 29 | 15 |
| Liponic EG-7 | 3 | 5 | 5 | 1 | 3 | 1 | 3 |
| Millithix 925 | 3 | 1 | 1 | 5 | 3 | 3 | 3 |
| Anhydrous Borax | 0.5 | 9.5 | 2.5 | 0.5 | 0.5 | 3.5 | 1.9 |
| Fragrance | 1 | 1 | 1 | 1 | 1 | 1 | 1 |
| Macol 57 | 0.5 | 0.5 | 0.5 | 0.5 | 0.5 | 0.5 | 0.5 |
| Pluronic F77 | 1.4 | 1.4 | 1.4 | 1.4 | 1.4 | 0.4 | — |
| Amersil DMC 357 | 0.5 | 0.5 | 0.5 | 0.5 | 0.5 | 0.5 | 0.5 |
| F, D & C Blue No. 1 | 0.1 | 0.1 | 0.1 | 0.1 | 0.1 | 0.1 | 0.1 |

Although this invention has been described with reference to specific Examples, it will be apparent to one skilled in the art that various modifications will be suggested, all of which are within the spirit and purview of this invention.

What is claimed is:

1. An antiperspirant composition comprising:

(i) from about 1 to about 50% by weight of an astringent antiperspirant-active salt;

(ii) from about 5 to about 60% of a $C_2$–$C_{12}$ polyhydric alcohol;

(iii) from about 0.5 to about 10% of dibenzyl monosorbitol acetal; and (iv) from about 0.1 to about 20% of a borate salt, wherein the composition has a pH of at least 4.3.

2. A composition according to claim 1, wherein the borate salt is anhydrous borax.

3. A composition according to claim 1, further comprising from about 0.1 to about 10% by weight of zinc glycinate.

4. A composition according to claim 1, wherein the polyhydric alcohol is selected from the group consisting of dipropylene glycol and propylene glycol.

* * * * *